(12) United States Patent
Vaillancourt et al.

(10) Patent No.: US 6,693,114 B2
(45) Date of Patent: Feb. 17, 2004

(54) 4-OXO-1,4-DIHYDRO[1,8]NAPHTHYRIDINE-3-CARBOXAMIDES AS ANTIVIRAL AGENTS

(75) Inventors: Valerie A. Vaillancourt, Kalamazoo, MI (US); Atli Thorarensen, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/151,439

(22) Filed: May 20, 2002

(65) Prior Publication Data

US 2002/0177604 A1 Nov. 28, 2002

Related U.S. Application Data

(62) Division of application No. 09/808,757, filed on Mar. 15, 2001, now Pat. No. 6,451,811.
(60) Provisional application No. 60/190,979, filed on Mar. 21, 2000.

(51) Int. Cl.[7] .............................................. A61K 41/435
(52) U.S. Cl. ...................................................... 514/300
(58) Field of Search ......................................... 514/300

(56) References Cited

U.S. PATENT DOCUMENTS

| | | | |
|---|---|---|---|
| 4,559,157 A | 12/1985 | Smith et al. ................... 252/90 |
| 4,568,649 A | 2/1986 | Bertoglio-Matte .......... 436/534 |
| 4,608,392 A | 8/1986 | Jacquet ....................... 514/844 |
| 4,820,508 A | 4/1989 | Wortzman .................... 424/59 |
| 4,826,837 A | 5/1989 | Doria et al. ................. 514/248 |
| 4,886,800 A | 12/1989 | Resch ...................... 514/234.5 |
| 4,938,949 A | 7/1990 | Borch et al. .................. 424/10 |
| 4,959,363 A | 9/1990 | Wentland .................. 514/234.5 |
| 4,992,478 A | 2/1991 | Geria ......................... 514/782 |
| 5,753,666 A | 5/1998 | Beasley et al. ............. 514/258 |
| 5,891,878 A | 4/1999 | Beasley et al. ............. 514/247 |

FOREIGN PATENT DOCUMENTS

| | | | |
|---|---|---|---|
| EP | 0 978 516 A1 | 2/2000 | ......... C07D/471/04 |
| WO | WO97/04775 | 2/1997 | ......... A61K/31/435 |
| WO | WO98/11073 | 3/1998 | ......... C07D/215/48 |
| WO | WO99/07704 | 2/1999 | ......... C07D/471/04 |
| WO | WO99/32450 | 7/1999 | ......... C07D/215/56 |
| WO | WO99/38867 | 8/1999 | ......... C07D/471/04 |

OTHER PUBLICATIONS

Cook, N.D., et. al., *Pharmaceutical Manufacturing International*, pp. 49–53, 1992.

Takeuchi, *Laboratory Practice*. Sep., 1992.

Vaillancourt, Valerie, "Naphthalene Carboxamides as Inhibitors of Human Cytomegalovirus DNA Polymerase." *Bioorganic and Medicinal Chemistry Letters*. Oxford, Great Britain. vol. 10, No. 18, pp. 2079–2081, Sep. 2000.

Wentland, et. al. "3–Quinolinecarboxamides. A series of Novel Orally–Active Antiherpetic Agents." *Journal of Medicinal Chemistry*. American Chemical Society. Washington, USA. vol. 36, No. 11, pp. 1580–1596.

Primary Examiner—Bernard Dentz
(74) Attorney, Agent, or Firm—Lucy X. Yang

(57) ABSTRACT

A compound of formula III:

or a pharmaceutically acceptable salt thereof wherein, the variables are as in the specification is provided. The compounds are particularly effective in the treatment or prevention of herpes viruses.

8 Claims, No Drawings

4-OXO-1,4-DIHYDRO[1,8]NAPHTHYRIDINE-3-CARBOXAMIDES AS ANTIVIRAL AGENTS

CROSS-REFERENCE TO RELATED APPLICATIONS

This application is a divisional application of U.S. patent application Ser. No. 09/808,757, filed Mar. 15, 2001 now U.S. Pat. No. 6,451,811 which claims the benefit of provisional application U.S. Ser. No. 60/190,979, filed Mar. 21, 2000.

BACKGROUND OF THE INVENTION

1. Field of the Invention

The present invention provides novel 1,8-naphthyridines, which are useful as antiviral agents (e.g. as agents against viruses of the herpes family).

2. Technology Description

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infections mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

U.S. Pat. No. 4,826,837 discloses 4-hydroxycinnoline-3-carboxamides and their use for the treatment of neoplastic diseases and acute and chronic infections of both bacterial and viral origin in mammals.

U.S. Pat. No. 4,886,800 discloses 4-substituted-cinnoline-3-carboxylic acids and 3-acyl-4-substituted-cinnoline derivatives and their use as central nervous system depressants.

U.S. Pat. Nos. 5,753,666 and 5,891,878 and WO 97/04775 disclose 1-alkyl-substituted-quinolone-3-carboxamides that are alleged to have therapeutic utility via inhibition of Phosphodiesterase IV esterase and/or Tumor Necrosis factor activity.

WO 99/38867 discloses 1-cycloalkyl-1,8-naphthyridin-4-one derivatives; pharmacologically acceptable salts or solvates thereof; and a phosphodiesterase IV inhibitor containing any of the above as an active ingredient.

WO 99/07704 discloses N-1-aryl and heteroaryl 1,8 naphthyridines as phosphodiesterase IV inhibitors.

Commonly assigned PCT/US98/25192 discloses 4-hydroxyquinoline-3-carboxamides and hydrazides as antiviral agents.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided. More specifically, the compounds are 4-oxo-1,4-dihydro[1,8]naphthyridine-3-carboxamides which are useful as antiviral agents, particularly against herpes viruses.

Even more specifically, the compounds are of formula (III)

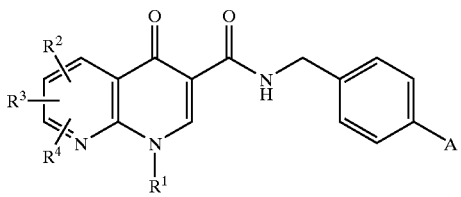

or a pharmaceutically acceptable salt thereof wherein,

A is
  (a) Cl,
  (b) Br,
  (c) CN,
  (d) $NO_2$, or
  (e) F;

$R^1$ is
  (a) $R^5$,
  (b) $NR^7R^8$, or
  (c) $SO_2R^9$;

$R^2$ is
  (a) aryl,
  (b) het,
  (c) $SO_mR^6$,
  (d) $OC_{2-7}$ alkyl substituted by OH,
  (e) $SC_{2-7}$ alkyl substituted by OH, or
  (f) $C_{2-8}$ alkyl which is partially unsaturated and is optionally substituted by one or more substituents selected from $R^{11}$, $OR^{13}$, $SR^{13}$, $NR^7R^8$, halo, (C=O)$C_{1-7}$ alkyl or $SO_mR^9$;
  with the proviso that when $R^1$=$R^5$=$(CH_2CH_2O)_tR^{10}$, then $R^2$ may additionally represent
  (a) H,
  (b) halo,
  (c) (C=O)$R^6$,
  (d) (C=O)$OR^9$,
  (e) cyano.
  (f) $OR^{10}$,
  (g) Ohet,
  (h) $NR^7R^8$,
  (i) $SR^{10}$,
  (j) Shet,
  (k) $NHCOR^{12}$,
  (l) $NHSO_2R^{12}$; or
  (m) $R^2$ together with $R^3$ or $R^4$ form a carbocyclic or het which may be optionally substituted by $NR^7R^8$, or $C_{1-7}$alkyl which may be optionally substituted by $OR^{14}$;

$R^3$ and $R^4$ are independently:
  (a) H,
  (b) halo,
  (c) aryl,
  (d) $S(O)_mR^6$,
  (e) (C=O)$R^6$,
  (f) (C=O)$OR^9$,
  (g) cyano, (h) het, wherein said het is bound via a carbon atom,
(i) $OR^{10}$,
(j) Ohet,
(k) $NR^7R^8$,
(l) $SR^{10}$,
(m) Shet,
(n) $NHCOR^{12}$,
(o) $NHSO_2R^{12}$,
(p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, (C=O)$C_{1-7}$alkyl, or $SO_mR^9$, or
(q) $R^4$ together with $R^3$ form a carbocyclic or het which may be optionally substituted by $NR^7R^8$, or $C_{1-7}$alkyl which may be optionally substituted by $OR^{14}$;

$R^5$ is
(a) $(CH_2CH_2O)_iR^{10}$,
(b) het, wherein said het is bound via a carbon atom,
(c) aryl,
(d) $C_{1-7}$alkyl which may be partially unsaturated and is optionally substituted by one or more substituents selected from $NR^7R^8$, $R^{11}$, $SO_mR^9$, or $OC_{2-4}$alkyl which may be further substituted by het, $OR^{10}$, or $NR^7R^8$, or
(e) $C_{3-8}$cycloalkyl which may be partially unsaturated and optionally substituted by one or more substituents selected from $R^{11}$, $NR^7R^8$, $SO_mR^9$, or $C_{1-7}$alkyl optionally substituted by $R^{11}$, $NR^7R^8$, or $SO_mR^9$;

$R^6$ is
(a) $C_{1-7}$alkyl,
(b) $NR^7R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from $NR^{10}R^{10}$, $R^{11}$, $SO_mR^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
(a) H,
(b) methyl, or
(c) $C_{2-7}$alkyl optionally substituted by OH;

$R^{11}$ is
(a) $OR^{10}$,
(b) Ohet,
(c) Oaryl,
(d) $CO_2R^{10}$,
(e) het,
(f) aryl, or
(g) CN;

$R^{12}$ is
(a) H,
(b) het,
(c) aryl,
(d) $C_{3-8}$cycloalkyl,
(e) methyl, or
(f) $C_{2-7}$alkyl optionally substituted by $NR^7R^8$ or $R^{11}$;

$R^{13}$ is
(a) $(P=O)(OR^{14})_2$,
(b) $CO(CH_2)_nCON(CH_3)-(CH_2)_nSO_3^-M^+$,
(c) an amino acid,
(d) C(=O)aryl, or
(e) C(=O)$C_{1-7}$alkyl optionally substituted by $NR^7R^8$, aryl, het, $CO_2H$, or $O(CH_2)_nCO_2R^{14}$;

$R^{14}$ is
(a) H, or
(b) $C_{1-7}$alkyl;

each i is independently 2, 3, or 4;

each n is independently 1, 2, 3, 4 or 5;

each m is independently 0, 1, or 2;

M is sodium, potassium, or lithium;

aryl is a phenyl radical or an ortho-fused bicyclic carbocyclic radical wherein at least one ring is aromatic;

wherein any aryl is optionally substituted with one or more substituents selected from halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;

het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;

wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$, $OR^{14}$, or $CO_2R^{14}$ groups.

In particularly preferred embodiments, $R_2$ is either alkynl-$CH_2OH$ or $(CH_2)_3OH$.

Another embodiment of the present invention provides a pharmaceutical composition comprising a compound of formula (III) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (IIIa)

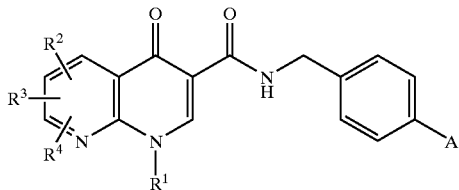

IIIa or a pharmaceutically acceptable salt thereof wherein,

A is
  (a) Cl,
  (b) Br,
  (c) CN,
  (d) $NO_2$, or
  (e) F;

$R^1$ is
  (a) $R^5$,
  (b) $NR^7R^8$, or
  (c) $SO_2R^9$;

$R^2$, $R^3$ and $R^4$ are independently:
  (a) H,
  (b) halo,
  (c) aryl,
  (d) $S(O)_mR^6$,
  (e) $(C=O)R^6$,
  (f) $(C=O)OR^9$,
  (g) cyano,
  (h) het, wherein said het is bound via a carbon atom,
  (i) $OR^{10}$,
  (j) Ohet,
  (k) $NR^7R^8$,
  (l) $SR^{10}$,
  (m) Shet,
  (n) $NHCOR^{12}$,
  (o) $NHSO_2R^{12}$,
  (p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$, or
  (q) $R^4$ together with $R^3$ form a carbocyclic or het which may be optionally substituted by $NR^7R^8$, or $C_{1-7}$alkyl which may be optionally substituted by $OR^{14}$;

$R^5$ is
  (a) $(CH_2CH_2O)_iR^{10}$,
  (b) het, wherein said het is bound via a carbon atom,
  (c) aryl,
  (d) $C_{1-7}$alkyl which may be partially unsaturated and is optionally substituted by one or more substituents selected from $NR^7R^8$, $R^{11}$, $SO_mR^9$, or $OC_{2-4}$alkyl which may be further substituted by het, $OR^{10}$, or $NR^7R^8$, or
  (e) $C_{3-8}$cycloalkyl which may be partially unsaturated and optionally substituted by one or more substituents selected from $R^{11}$, $NR^7R^8$, $SO_mR^9$, or $C_{1-7}$alkyl optionally substituted by $R^{11}$, $NR^7R^8$, or $SO_mR^9$;

$R^6$ is
  (a) $C_{1-7}$alkyl,
  (b) $NR^7R^8$,
  (c) aryl, or
  (d) het, wherein said het is bound via a carbon atom;

$R^7$ and $R^8$ are independently
  (a) H,
  (b) aryl,
  (c) $C_{1-7}$alkyl which may be partially unsaturated and is optionally substituted by one or more substituents selected from $NR^{10}R^{10}$, $R^{11}$, $SO_mR^9$, $CONR^{10}R^{10}$, or halo, or,
  (d) $R^7$ and $R^8$ together with the nitrogen to which they are attached form a het;

$R^9$ is
  (a) aryl,
  (b) het,
  (c) $C_{3-8}$cycloalkyl,
  (d) methyl, or
  (e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
  (a) H,
  (b) methyl, or
  (c) $C_{2-7}$alkyl optionally substituted by OH;

$R^{11}$ is
  (a) $OR^{10}$,
  (b) Ohet,
  (c) Oaryl,
  (d) $CO_2R^{10}$,
  (e) het,
  (f) aryl, or
  (g) CN;

$R^{12}$ is
  (a) H,
  (b) het,
  (c) aryl,
  (d) $C_{3-8}$cycloalkyl,
  (e) methyl, or
  (f) $C_{2-7}$alkyl optionally substituted by $NR^7R^8$ or $R^{11}$;

$R^{13}$ is
  (a) $(P=O)(OR^{14})_2$,
  (b) $CO(CH_2)_nCON(CH_3)-(CH_2)_nSO_3^-M^+$,
  (c) an amino acid,
  (d) $C(=O)$aryl, or
  (e) $C(=O)C_{1-7}$alkyl optionally substituted by $NR^7R^8$, aryl, het, $CO_2H$, or $O(CH_2)_nCO_2R^{14}$;

$R^{14}$ is
  (a) H, or
  (b) $C_{1-7}$alkyl;

each i is independently 2, 3, or 4;
each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from halo, OH, cyano, $CO_2R^{14}$, $CF_3$, $C_{1-6}$alkoxy, and $C_{1-6}$ alkyl which may be further substituted by one to three $SR^{14}$, $NR^{14}R^{14}$, $OR^{14}$, or $CO_2R^{14}$ groups;

het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$ alkyl which may be further substituted by one to three $SR^{14}$, $NR^{14}R^{14}$, $OR^{14}$, or $CO_2R^{14}$ groups.

A further embodiment of the present invention comprises the use of a compound of formula (III) or of formula (IIIa) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (III) or of formula (IIIa) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical wherein at least one ring is aromatic. Het is a four- (4), five- (5), six- (6), or seven- (7) membered saturated or unsaturated ring containing 1, 2 or 3 heteroatoms selected from the group consisting of non-peroxide oxygen, sulfur, and nitrogen, which is optionally fused to a benzene ring, or any bicyclic heterocyclic group. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

To the extent that any pharmaceutically active compound is disclosed or claimed, it is expressly intended to include all active metabolites produced in vivo.

The carbon atom content of various hydrocarbon-containing moieties is indicated by a prefix designating a lower and upper number of carbon atoms in the moiety, i.e., the prefix $C_{i-j}$ indicates a moiety of the integer 'i' to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, 'Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (III) having any combination of the values, specific values, more specific values, and preferred values described herein.

2. The Invention

The present invention provides compounds of formula (III):

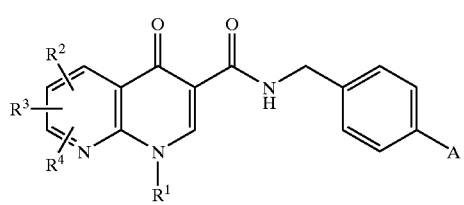

or a pharmaceutically acceptable salt thereof wherein,

A is
  (a) Cl,
  (b) Br,
  (c) CN,
  (d) $NO_2$, or
  (e) F;

$R^1$ is
  (a) $R^5$,
  (b) $NR^7R^8$, or
  (c) $SO_2R^9$;

$R^2$ is
  (a) aryl,
  (b) het,
  (c) $SO_mR^6$
  (d) $OC_{2-7}$ alkyl substituted by OH,
  (e) $SC_{2-7}$ alkyl substituted by OH, or
  (f) $C_{2-8}$ alkyl which is partially unsaturated and is optionally substituted by one or more substituents selected from a group consisting of $R^{11}$, $OR^{13}$, $SR^{13}$, $NR^7R^8$, halo, $(C=O)C_{1-7}$alkyl or $SO_mR^9$;
  with the proviso that when $R^1=R^5=(CH_2CH_2O)_rR^{10}$, then $R^2$ may additionally represent
  (a) H,
  (b) halo,
  (c) $(C=O)R^6$, (d) (C=O)OR$^9$,
(e) cyano,
(f) OR$^{10}$,
(g) Ohet,
(h) NR$^7$R$^8$,
(i) SR$^{10}$,
(j) Shet,
(k) NHCOR$^{12}$,
(l) NHSO$_2$R$^{12}$; or
(m) R$^2$ together with R$^3$ or R$^4$ form a carbocyclic or het which may be optionally substituted by NR$^7$R$^8$, or C$_{1-7}$alkyl which may be optionally substituted by OR$^{14}$;

R$^3$ and R$^4$ are independently:
(a) H,
(b) halo,
(c) aryl,
(d) S(O)$_m$R$^6$,
(e) (C=O)R$^6$,
(f) (C=O)OR$^9$,
(g) cyano,
(h) het, wherein said het is bound via a carbon atom.
(i) OR$^{10}$,
(j) Ohet,
(k) NR$^7$R$^8$,
(l) SR$^{10}$,
(m) Shet,
(n) NHCOR$^{12}$,
(o) NHSO$_2$R$^{12}$,
(p) C$_{1-7}$alkyl which may be partially unsaturated and optionally substituted by one or more substituents of the group R$^{11}$, OR$^{13}$, SR$^{10}$, SR$^{13}$, NR$^7$R$^8$, halo, (C=O)C$_{1-7}$alkyl, or SO$_m$R$^9$,
(q) R$^4$ together with R$^3$ form a carbocyclic or het which may be optionally substituted by NR$^7$R$^8$, or C$_{1-7}$alkyl which may be optionally substituted by OR$^{14}$;

R$^5$ is
(a) (CH$_2$CH$_2$O)$_i$R$^{10}$,
(b) het, wherein said het is bound via a carbon atom,
(c) aryl,
(d) C$_{1-7}$alkyl which may be partially unsaturated and is optionally substituted by one or more substituents selected from NR$^7$R$^8$, R$^{11}$, SO$_m$R$^9$, or OC$_{2-4}$alkyl which may be further substituted by het, OR$^{10}$, or NR$^7$R$^8$, or
(e) C$_{3-8}$cycloalkyl which may be partially unsaturated and optionally substituted by one or more substituents selected from R$^{11}$, NR$^7$R$^8$, SO$_m$R$^9$, or C$_{1-7}$alkyl optionally substituted by R$^{11}$, NR$^7$R$^8$, or SO$_m$R$^9$;

R$^6$ is
(a) C$_{1-7}$alkyl,
(b) NR$^7$R$^8$,
(c) aryl, or
(d) het, wherein said het is bound via a carbon atom;

R$^7$ and R$^8$ are independently
(a) H,
(b) aryl,
(c) C$_{1-7}$alkyl which may be partially unsaturated and is optionally substituted by one or more substituents selected from NR$^{10}$R$^{10}$, R$^{11}$, SO$_m$R$^9$, CONR$^{10}$R$^{10}$, or halo, or,
(d) R$^7$ and R$^8$ together with the nitrogen to which they are attached form a het;

R$^9$ is
(a) aryl,
(b) het,
(c) C$_{3-8}$cycloalkyl,
(d) methyl, or
(e) C$_{2-7}$alkyl which may be partially unsaturated and is optionally substituted by one or more substituents selected from NR$^{10}$R$^{10}$, R$^{11}$, SH, CONR$^{10}$R$^{10}$, or halo;

R$^{10}$ is
(a) H,
(b) methyl, or
(c) C$_{2-7}$alkyl optionally substituted by OH;

R$^{11}$ is
(a) OR$^{10}$,
(b) Ohet,
(c) Oaryl,
(d) CO$_2$R$^{10}$,
(e) het,
(f) aryl, or
(g) CN;

R$^{12}$ is
(a) H,
(b) het,
(c) aryl,
(d) C$_{3-8}$cycloalkyl,
(e) methyl, or
(f) C$_{2-7}$alkyl optionally substituted by NR$^7$R$^8$ or R$^{11}$;

R$^{13}$ is
(a) (P=O)(OR$^{14}$)$_2$,
(b) CO(CH$_2$)$_n$CON(CH$_3$)—(CH$_2$)$_n$SO$_3$$^-$M$^+$,
(c) an amino acid,
(d) C(=O)aryl, or
(e) C(=O)C$_{1-7}$alkyl optionally substituted by NR$^7$R$^8$, aryl, het, CO$_2$H, or O(CH$_2$)$_n$CO$_2$R$^{14}$;

R$^{14}$ is
(a) H, or
(b) C$_{1-7}$alkyl;

each i is independently 2, 3, or 4;
each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from halo, OH, cyano, CO$_2$R$^{14}$, CF$_3$, C$_{1-6}$alkoxy, and C$_{1-6}$ alkyl which maybe further substituted by one to three SR$^{14}$, NR$^{14}$R$^{14}$, OR$^{14}$, or CO$_2$R$^{14}$ groups;
het is a four- (4), five- (5), six- (6), or seven- (7) membered saturated or unsaturated heterocyclic ring having 1, 2, or 3 heteroatoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, CO$_2$R$^{14}$, CF$_3$, C$_{1-6}$alkoxy, oxo, oxime, and C$_{1-6}$ alkyl which maybe further substituted by one to three SR$^{14}$, NR$^{14}$R$^{14}$, OR$^{14}$, or CO$_2$R$^{14}$ groups.

Specifically, C$_{1-7}$alkyl can be methyl, ethyl, propyl, isopropyl, butyl, iso-butyl, sec-butyl, pentyl, 3-pentyl, hexyl, or heptyl; C$_{3-7}$cycloalkyl can be cyclopropyl, cyclobutyl, cyclopentyl, cyclohexyl, or cycloheptyl.

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

Particularly preferred compounds are those where A is Cl and $R^2$ is either alkynl-$CH_2OH$ or $(CH_2)_3OH$.

Specifically preferred compounds include, but are not limited to the following:

N-(4-chlorobenzyl)-6-(3-hydroxy-1-propynyl)-1,7-dimethyl-4-oxo-1,4-dihydro[1,8]naphthyridine-3-carboxamide; and N-(4-chlorobenzyl)-6-(3-hydroxy-1-propynyl)-7-methoxy-1-methyl-4-oxo-1,4-dihydro[1,8]naphthyridine-3-carboxamide.

Still another embodiment of the present invention provides a method for treating a disease or condition in a mammal caused by a viral infection, particularly a herpes viral infection, comprising administering to the mammal a therapeutically effective amount of a compound of formula (III) or (IIIa) as defined above or a pharmaceutically effective salt therof.

The following Charts 1–8 describe the preparation of the compounds of the present invention. All of the starting materials and final compounds are prepared by procedures described in these charts or by procedures analogous thereto, which would be well known to one of ordinary skill in organic chemistry. All of the variables used in the charts are as defined below or as in the claims.

The basic ring system can be prepared in several ways, one of which is shown in Chart 1. Condensation of a substituted 2-aminopyridine with diethyl ethoxymethylenemalonate and subsequent cyclization under thermal conditions provides the 1,8-naphthyridine-3-carboxylic ester. Treatment of this compound with an amine such as 4-chlorobenzylamine at elevated temperatures provides the 1,8-naphthyridine-3-carboxamide.

Chart 1

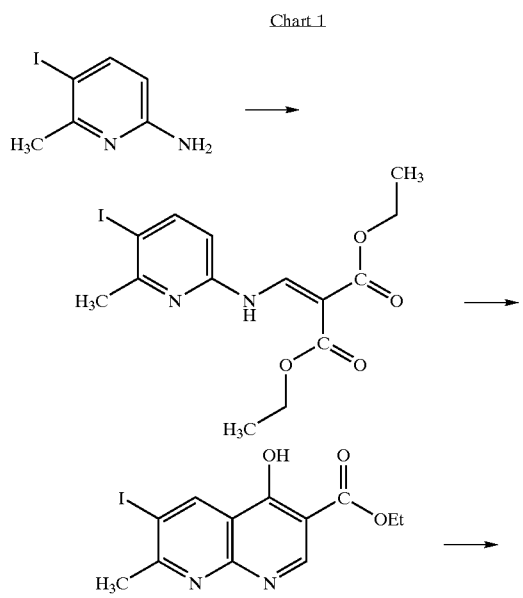

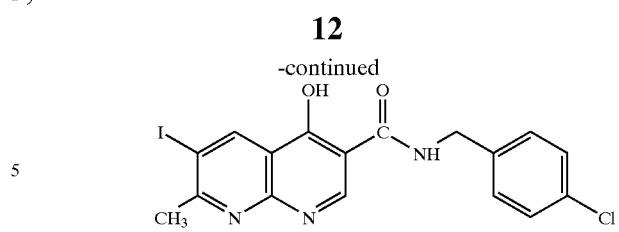

These ring systems can be further elaborated. One example of such an elaboration is shown in Chart 2. Palladium catalyzed coupling of the aryl iodide with an acetylene such as propargyl alcohol and subsequent reduction of the alkyne by hydrogenation provides the 6-(3-hydroxypropyl)-1,8-naphthyridine-3-carboxamide.

Chart 2

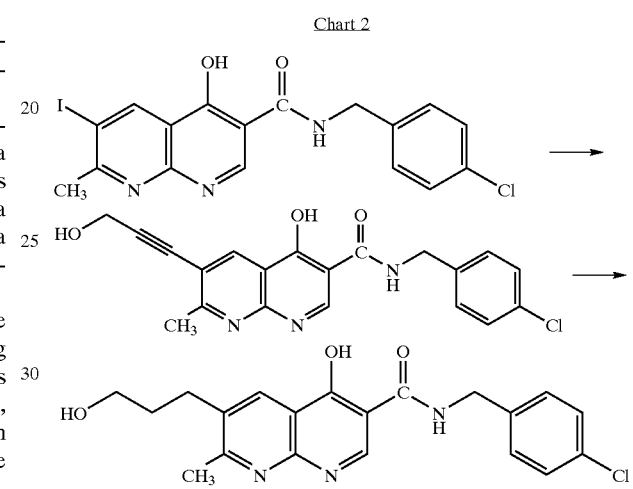

A second example of an elaboration is depicted in Chart 3. Palladium catalyzed carbomethylation of the aryl iodide provides the 6-methyl ester.

Chart 3

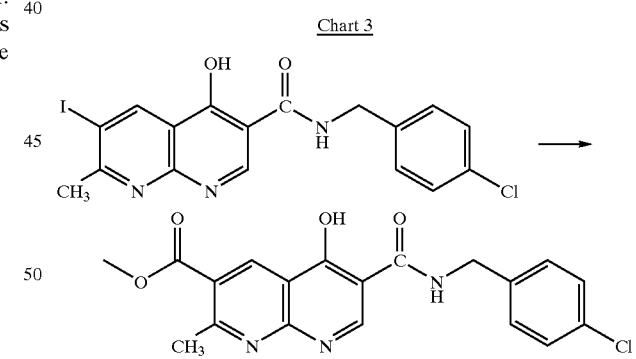

The above compounds can also be alkylated on the N–1 nitrogen by treatment with an alkyl halide and potassium or cesium carbonate in DMF (Chart 4).

Chart 4

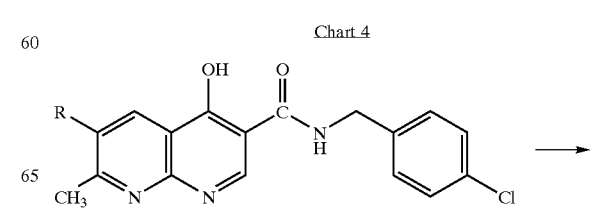

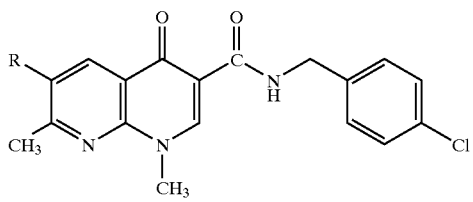

Alternatively, the N-1 substituent can be incorporated into the structure early in the synthetic sequence as shown in Chart 5. Beginning with an N-alkylated 2-aminopyridine, condensation with diethyl ethoxymethylenemalonate and cyclization by heating in Eaton's reagent provides the naphthyridine carboxylic ester. Saponification to the acid followed by activation of the acid and subsequent coupling with an amine such as 4-chlorobenzylamine provides the naphthyridine carboxamide.

CHART 5

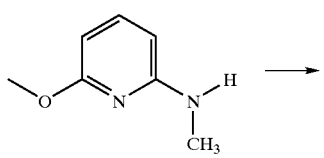

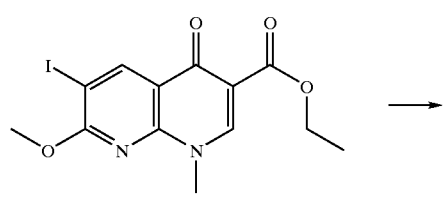

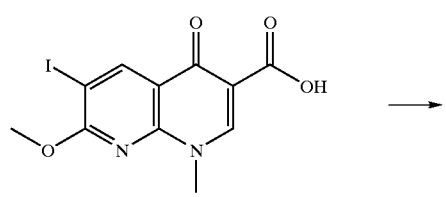

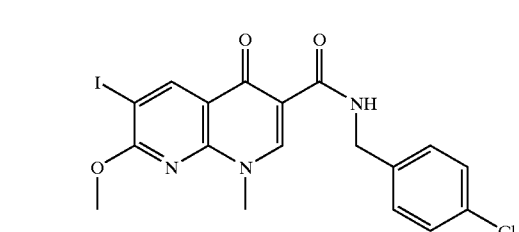

As above, these naphthyridine carboxamides can be further elaborated. Some examples of subsequent manipulations are shown in the charts below. Palladium-catalyzed coupling of an acetylene such as propargyl alcohol with the halogen-substituted naphthyridines (e.g. Chart 6) provides alkynyl-substituted analogs. Hydrogenation of these analogs with an appropriate catalyst such as palladium on carbon provides alkyl-substituted naphthyridine carboxamides.

CHART 6

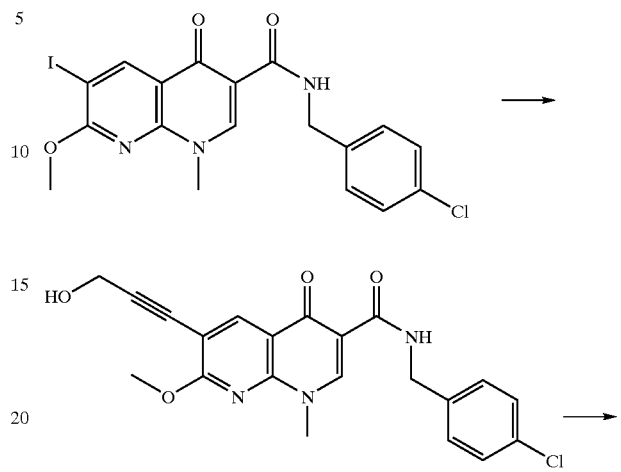

Another example of subsequent manipulations of the naphthyridine carboxamides is shown in Chart 7. Palladium-catalyzed carbonylation of the halogenated naphthyridines in the presence of methanol provides the corresponding esters.

CHART 7

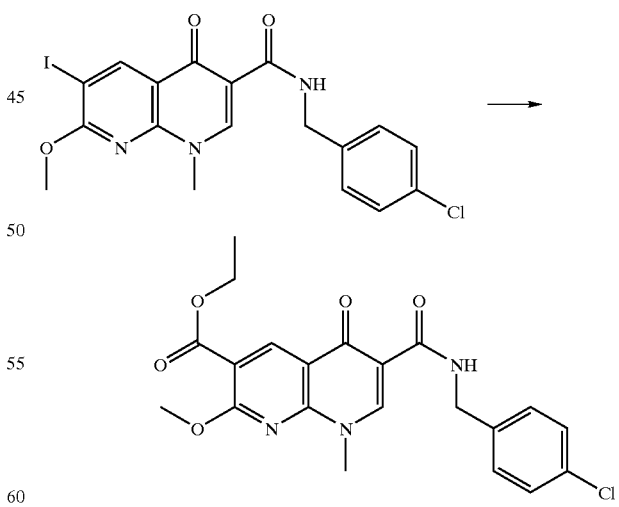

Additional possible manipulations of the cinnolines include reactions such as deprotection of methyl ethers (Chart 8). This can be accomplished by treatment with reagents such as pyridinium hydrochloride at elevated temperatures.

CHART 8

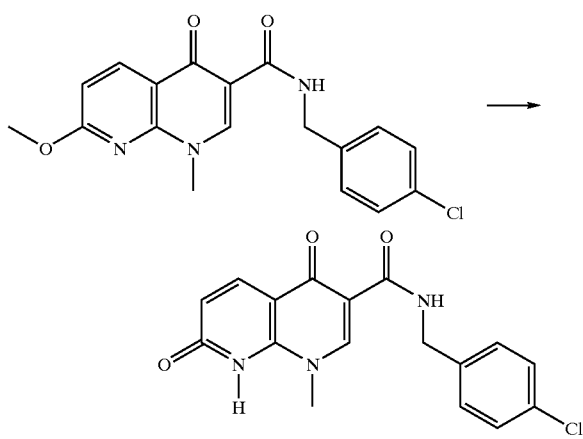

The inventive compounds of formula (III) or the compounds of formula (IIIa) may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). To the extent necessary for completion, this publication is expressly incorporated by reference. The compounds and compositions of the present invention can be administered parenterally (for example, by intravenous, intraperitoneal or intramuscular injection), topically, intranasally, orally, intravaginally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices such as those depending on osmotic delivery developed by ALZA Corp, under the OROS trademark.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, cyclodextrins, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (III) and (IIIa) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (III) and (IIIa) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula (III) or (IIIa) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock (e.g., food animals such as cows, pigs, sheep, goats, deer, etc.) and companion animals (e.g., dogs, cats, birds and horses) is also specifically contemplated as falling within the scope of the instant invention.

The invention will be further described by the following non-limiting examples.

Preparation 1

Ethyl 6-bromo-4-hydroxy-7-methyl[1,8]naphthyridine-3-carboxylate

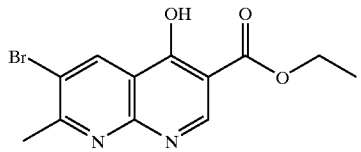

A solution of 6-amino-3-bromo-2-methylpyridine (1.89 g, 10 mmol) and diethoxymethylenemalonate (2.16 g, 10 mmol) is heated at 110° C. for 30 min. The reaction is cooled and the residue is recrystallized from EtOH. To the resulting solid is dissolved in 45 mL of $Ph_2O$. The mixture is heated to 250° C. for 3 h. The solution is then cooled to room temperature and the resulting precipitate is collected and dried. The crude product is chromatographed on silica (Biotage flash 40M, 2% $MeOH/CH_2Cl_2$ eluent). Fractions homogeneous by TLC are collected and concentrated to yield 1.075 g (35%) of the desired product as a yellow solid. Physical data are as follows: m.p. 270° C. (dec.); $^1$H NMR (DMSO-$d_6$) δ12.73, 8.49, 8.47, 4.21, 2.67, 1.27.

Preparation 2

6-bromo-N-(4-chlorobenzyl)-4-hydroxy-7-methyl[1,8]naphthyridine-3-carboxamide

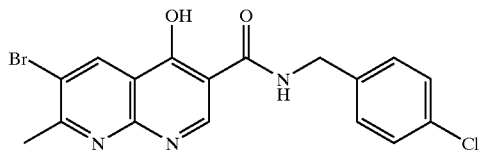

A solution of ethyl 6-bromo-4-hydroxy-7-methyl[1,8]naphthyridine-3-carboxylate (0.57 g, 1.83 mmol) and 4-chlorobenzylamine (2.59 g, 18.30 mmol) is heated to 180° C. for 1 h. The mixture is cooled and diluted with EtOAc. The resulting precipitate is collected and dried. Physical characteristics are as follows: m.p. 269–270° C.; $^1$H NMR (DMSO-$d_6$) δ13.21, 10.09, 8.67, 8.62, 7.38, 4.54, 2.71; IR (drift) 3028, 2974, 2907, 1653, 1598, 1555, 1526, 1493, 1410, 1354, 1326, 1242, 1096, 806, 639 $cm^{-1}$; Anal. Calcd for $C_{17}H_{13}BrClN_3O_2$: C, 50.21; H, 3.22; N, 10.33; Found: C, 50.31; H, 3.23; N, 10.17.

EXAMPLE 1

6-bromo-N-(4-chlorobenzyl)-1,7-dimethyl-4-oxo-1,4-dihydro[1,8]naphthyridine-3-carboxamide

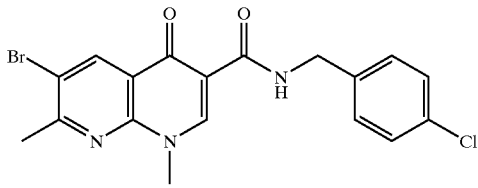
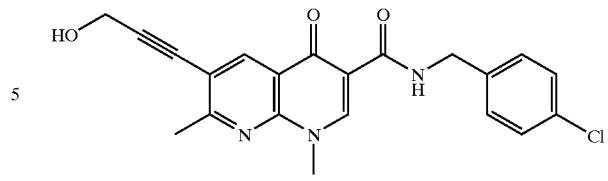

To a solution of 6-bromo-N-(4-chlorobenzyl)4-hydroxy-7-methyl[1,8]naphthyridine-3-carboxamide (0.400 g, 0.98 mmol) and potassium carbonate (0.54 g, 3.92 mmol) in 5 mL DMF at room temperature is added dropwise methyl iodide (0.167 g, 1.18 mmol). The mixture is stirred at room temperature for 30 min then diluted with water. The resulting solid is filtered, washed with water and dried. The crude product is triturated with EtOAc/hexanes to yield 0.358 g (85%) of the desired product as a white solid. Physical characteristics are as follows: m.p. 266–268° C.; $^1$H NMR (CDCl$_3$) δ10.18, 8.92, 8.83, 7.30, 4.65, 4.03, 2.82; Anal. Calcd for $C_{18}H_{15}BrClN_3O_2$: C, 51.39; H, 3.59; N, 9.99; Found: C, 51.02; H, 3.57; N, 9.94.

Preparation 3

N-(4-chlorobenzyl)-4-hydroxy-6-(3-hydroxy-1-propynyl)-7-methyl[1,8]naphthyridine-3-carboxamide

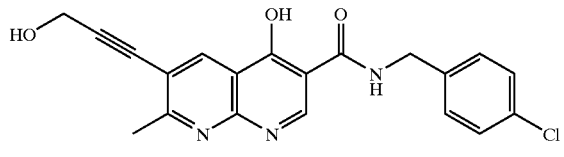

A solution of 6-bromo-N-(4-chlorobenzyl)-4-hydroxy-7-methyl[1,8]naphthyridine-3-carboxamide (0.244 g, 0.60 mmol), propargyl alcohol (0.047 g, 0.84 mmol), triethylamine (0.38 mL) and PdCl$_2$(PPh$_3$)$_2$ (0.023 g, 0.03 mmol) in 3 mL DMF is heated to 90° C. for 2.5 h. The resulting solution is cooled and partitioned between EtOAc and water. The solid which formed is filtered and discarded. The aqueous layer is extracted with EtOAc (3×). The combined organic layers are washed with brine, dried and condensed. The crude product is chromatographed on silica (Biotage flash 40S, eluent 2% MeOH/CH$_2$Cl$_2$ then 3% MeOH/CH$_2$Cl$_2$. Fractions homogeneous by TLC are combined and condensed to yield 0.081 g (35%) of the desired product as a yellow solid. Physical characteristics are as follows: m.p. 279–281° C. (dec.); $^1$H NMR (DMSO-d$_6$) δ13.19, 10.12, 8.64, 8.43, 7.38, 5.46, 4.54, 4.40, 2.71; IR (drift) 3194, 3065, 2944, 1645, 1597, 1566, 1522, 1488, 1418, 1357, 1257, 1208, 1015, 851, 809 cm$^{-1}$; OAMS supporting ions at: ESI+ 381.9 ESI− 379.9; HRMS (FAB) calcd for $C_{20}H_{16}ClN_3O_3$ +H$_1$ 382.0958, found 382.0960.

EXAMPLE 2

N-(4-chlorobenzyl)-6-(3-hydroxy-1-propynyl)-1,7-dimethyl-4-oxo-1,4-dihydro[1,8]naphthyridine-3-carboxamide To a mixture of the N-(4-chlorobenzyl)-4-hydroxy-6-(3-hydroxy-1-propynyl)-7-methyl[1,8]naphthyridine-3-carboxamide (0.081 g, 0.212 mmol) and potassium carbonate (0.117 g, 0.848 mmol) in 5 mL DMF is added methyl iodide (0.036 g, 0.254 mmol). The mixture is stirred at room temperature for 30 min then diluted with water. The resulting precipitate is filtered and dried. The crude solid is triturated with EtOAc/hexanes to yield 0.072 g (86%) of the desired product as a pale yellow solid. Physical characteristics are as follows: m.p. 217–218° C.; $^1$H NMR (DMSO-d$_6$) δ10.13, 8.99, 8.46, 7.39, 5.47, 4.55, 4.40, 3.99, 2.75; IR (drift) 3395, 1661, 1604, 1561, 1544, 1503, 1413, 1357, 1261, 1032, 1017, 842, 811, 800, 601 cm$^{-1}$; MS (EI) m/z (rel. intensity) 395 (M$^+$, 8), 255 (29), 229 (17), 228 (99), 198 (41), 169 (14), 140 (54), 89 (15), 77 (14), 73 (22), 73 (17); HRMS (FAB) calcd for $C_{21}H_{18}ClN_3O_3$ +H$_1$ 396.1115, found 396.1121.

EXAMPLE 3

N-(4-chlorobenzyl)-6-(3-hydroxypropyl)-1,7-dimethyl-4-oxo-1,4-dihydro[1,8]naphthyridine-3-carboxamide

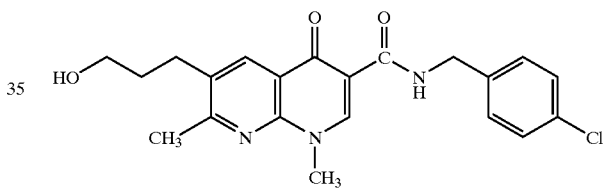

To a solution of N-(4-chlorobenzyl)-6-(3-hydroxy-1-propynyl)-1,7-dimethyl4-oxo-1,4-dihydro[1,8]naphthyridine-3-carboxamide (0.12 g, 0.30 mmol) in CH$_2$Cl$_2$ (20 mL) and MeOH (3 mL) is added 10% Pd/C (21 mg). The reaction is subjected to hydrogenation at 18 psi for 30 min. The reaction is filtered over Celite and monitored to determine the extent of the reaction. Fresh catalyst is added and the reaction is placed under hydrogen at 18 psi again. After another 30 minutes, the reaction is complete. The reaction is filtered over Celite. The filter cake is rinsed thoroughly with CH$_2$Cl$_2$, and MeOH. The filtrate is concentrated in vacuo and the residue is then dissolved in CH$_2$Cl$_2$ and adsorbed onto silica. Purification by chromatography (eluent 1% MeOH/CH$_2$Cl$_2$ (1 L), 2% MeOH/CH$_2$Cl$_2$ (1 L), 4% MeOH/CH$_2$Cl$_2$ (1 L)) affords the desired product as a white solid (0.079 g, 0.20 mmol, 66%). Physical characteristics are as follows: m.p. 176–177° C.; $^1$H NMR (300 MHz, DMSO-d$_6$) δ10.30, 8.98, 8.35, 7.41, 7.36, 4.59, 4.56, 4.01, 3.47, 2.82, 2.67, 1.75; IR (drift) 1658, 1609, 1556, 1531, 1503, 1458, 1420, 1357, 1333, 1260, 1095, 1056, 1017, 811, 701 cm$^{-1}$; MS (ESI) m/z 400.1 (M+H)$^+$, 398.1 (M-H); HRMS (FAB) calcd for $C_{21}H_{22}ClN_3O_3$+H$_1$ 400.1428, found 400.1434.

Preparation 4

Ethyl 6-iodo-7-methoxy-1-methyl-4-oxo-1,4-dihydro[1,8]naphthyridine-3-carboxylate

21

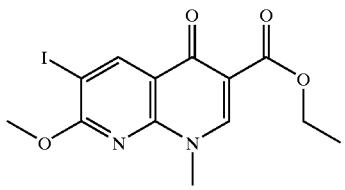

6-Methoxy-N-methyl-2-pyridinamine (17.24 g, 124 mmol) is dissolved in DMF (160 mL) and cooled to 0° C. followed by the addition of NIS (28 g, 124 mmol, 1 equiv), at a rate which keeps the reaction temperature below 10° C. The reaction is then allowed to warm to room temperature and stirred for 1 h. The reaction is distilled to dryness in vacuo and the residue is dissolved in $CH_2Cl_2$ and passed through a silica plug eluting with heptane/EtOAc (9/1) affording 32 g of crude 5-iodo-6-methoxy-N-methyl-2-pyridinamine. The crude 5-iodo-6-methoxy-N-methyl-2-pyridinamine is dissolved in diethyl ethoxymethylenemalonate (32 mL) and the mixture is heated at 140° C. for 2 h, then cooled to room temperature and passed through a silica plug eluting with heptane/EtOAc (19/1, 0/1). The product is then dissolved in Eaton's reagent (132 mL) and heated at 100° C. for 40 min, cooled to rt and poured into $Na_2CO_3$. The basic aqueous layer is then extracted with $CH_2Cl_2$ (3×), washed with water, and brine, dried ($MgSO_4$), filtered and concentrated in vacuo. The residue is purified by silica gel chromatography (heptane/EtOAc, 4/1, 1/1, $CH_2Cl_2$/MeOH 19/1) the desired product is then triturated with MeOH to afford 7.9 g (16%) of ethyl 6-iodo-7-methoxy-1-methyl-4-oxo-1,4-dihydro[1,8]naphthyridine-3-carboxylate. Physical characteristics are as follows: $^1$H NMR (CDCl) δ9.04, 8.52, 4.41, 4.13, 3.91, 1.43; IR (diffuse reflectance) 2491, 2427, 2350, 2282, 2242, 1678, 1632, 1613, 1579, 1384, 1309, 1275, 1227, 1106, 804, cm$^{-1}$; MS (EI) m/z 388, 344, 343, 317, 316, 185, 159, 86, 84, 51; Anal calcd for $C_{13}H_{13}IN_2O_4$: C, 40.23; H, 3.38; N, 7.22. Found: C, 40.20; H, 3.40; N, 7.16

Preparation 5
6-Iodo-7-methoxy-1-methyl-4-oxo-1,4-dihydro[1,8] naphthyridine-3-carboxylic acid

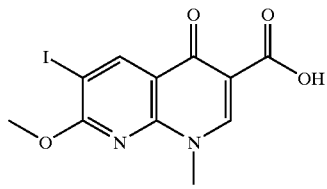

Ethyl 6-iodo-7-methoxy-1-methyl-4-oxo-1,4-dihydro[1,8]naphthyridine-3-carboxylate (3.63 g) is dissolved in MeOH (200 mL). To this is added 6N NaOH (60 mL) and the resulting mixture is stirred at room temperature for 4 h. The white suspension is poured into a seperatory funnel and the organic layer is made acidic with HCl, extracted several times with $CH_2Cl_2$ (total volume 4 L), washed with water, brine, dried ($MgSO_4$), filtered and concentrated in vacuo to afford 3.2 g (96%) of 6-iodo-7-methoxy-1-methyl-4-oxo-1,4-dihydro[1,8]naphthyridine-3-carboxylic acid. Physical characteristics are as follows:
$^1$H NMR (CDCl$_3$) δ14.62, 9.09, 8.81, 4.19, 4.05; IR (diffuse reflectance) 2497, 2350, 2338, 2086, 1990, 1720, 1716, 1628, 1525, 1482, 1464, 1448, 1385, 1278, 810, cm$^{-1}$; MS (EI) m/z 360, 316, 185, 159, 158, 142, 86, 84, 63, 53, 51; Anal calcd for $CH_{11}H_9IN_2O_4$: C, 36.69; H, 2.52; N, 7.78. Found: C, 36.93; H, 2.57; N, 7.77.

22
EXAMPLE 4
N-(4-Chlorobenzyl)-6-iodo-7-methoxy-1-methyl-4-oxo-1,4-dihydro[1,8]naphthyridine-3-carboxamide

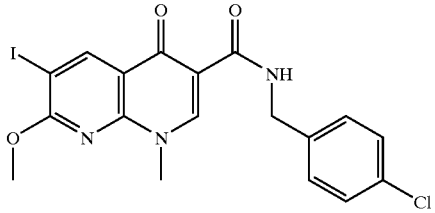

6-Iodo-7-methoxy-1-methyl-4-oxo-1,4-dihydro[1,8] naphthyridine-3-carboxylic acid (1.50 g) is dissolved in $CH_2Cl_2$ (0.5 L). To this is added diphenyl chloridophosphate (1.5 mL) and triethyl amine (1.7 mL). The resulting mixture is stirred at room temperature for 2 h, followed by the addition of 4-chlorobenzyl amine (1.2 mL). The reaction is stirred for additional 3 h, then washed with 1N HCl, 1N NaOH, brine, dried ($MgSO_4$), filtered and concentrated in vacuo. The residue is purified by silica gel chromatography (heptane/EtOAc 4/1, 1/1, $CH_2Cl_2$/MeOH 19/1) and the product is then triturated with MeOH to afford 592 mg (29%) of N-(4-chlorobenzyl)-6-iodo-7-methoxy-1-methyl-4-oxo-1,4-dihydro[1,8]naphthyridine-3-carboxamide. Physical characteristics are as follows: $^1$H NMR (CDCl$_3$) δ10.20, 9.01, 8.81, 7.32–7.27, 4.62, 4.13, 3.96; $^{13}$C NMR (CDCl$_3$) δ175.24, 164.41, 162.95, 159.66, 148.69, 147.78, 147.69, 137.26, 132.85, 128.93, 128.69, 118.76, 113.68, 55.77, 42.58, 39.12; IR (diffuse reflectance) 2296, 1908, 1665, 1613, 1593, 1570, 1544, 1507, 1491, 1460, 1447, 1386, 1286, 1278, 809, cm$^{-1}$; MS (FAB) m/z 484 (MH$^+$), 486, 485, 484, 344, 343, 217, 133, 127, 125, 55; Anal. calcd for $C_{18}H_{15}ClIN_3O_3$: C, 44.70; H, 3.13; N, 8.69. Found: C, 44.38; H, 3.17; N, 8.62.

EXAMPLE 5
N-(4-Chlorobenzyl)-1-methyl-4,7-dioxo-1,4,7,8-tetrahydro[1,8]naphthyridine-3-carboxamide

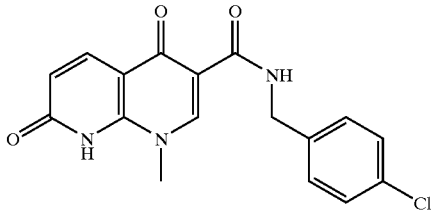

N-(4-Chlorobenzyl)-6-iodo-7-methoxy-1-methyl-4-oxo-1,4-dihydro[1,8]naphthyridine-3-carboxamide (150 mg) is mixed with pyridine hydrochloride (1.50 g). The resulting solid is heated at 200° C. for 1 h, then cooled to room temperature and washed with MeOH. The residue is then dissolved in $CH_2Cl_2$, washed with 1N HCl, brine, dried ($MgSO_4$), filtered and concentrated in vacuo. The crude product is purified by silica gel chromatography ($CH_2Cl_2$/MeOH 19/1, 9/1) to afford 60 mg (56%) of N-(4-chlorobenzyl)-1-methyl-4,7-dioxo-1,4,7,8-tetrahydro[1,8] naphthyridine-3-carboxamide. Physical characteristics are as follows: $^1$H NMR (DMSO-d$_6$) δ8.85, 8.44, 7.42–7.33, 6.82, 4.55, 3.92; IR (diffuse reflectance) 3044, 2350, 2318, 1941, 1908, 1679, 1645, 1627, 1553, 1524, 1504, 1466, 803, 672, 656, cm$^{-1}$.

MS (El) m/z 343 (M$^+$), 176, 86, 84, 80, 79, 78, 65, 64, 63, 61; HRMS (FAB) calcd for $C_{17}H_{14}ClN_3O_3+H_1$ 344.0802, found 344.0815.

EXAMPLE 6
N-(4-chlorobenzyl)-6-(3-hydroxy-1-propynyl)-7-methoxy-1-methyl-4-oxo-1,4-dihydro[1,8]naphthyridine-3-carboxamide

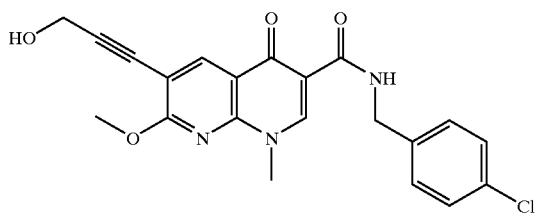

N-(4-chlorobenzyl)-6-iodo-7-methoxy-1-methyl-4-oxo-1,4-dihydro[1,8]naphthyridine-3-carboxamide (250 mg), copper iodide (40 mg) and dichlorobis(triphenylphosphine) palladium (30 mg) are dissolved in a mixture of diethylamine (15 mL) and THF (15 mL). To this is added propargyl alcohol (452 µL). The mixture is heated at reflux for 1 h, cooled to room temperature, diluted with $CH_2Cl_2$, washed with 1N HCl, brine, dried ($MgSO_4$) and concentrated in vacuo. The residue is purified by silica gel chromatography ($CH_2Cl_2$/MeOH 1/0, 45/1, 19/1, 9/1) and the resulting product is recrystalized from MeOH to afford 144 mg (68%) of N-(4-chlorobenzyl)-6-(3-hydroxy-1-propynyl)-7-methoxy-1-methyl-4-oxo-1,4-dihydro[1,8]naphthyridine-3-carboxamide. Physical characteristics are as follows: $^1$H NMR (CDCl$_3$) δ8.80, 8.60, 7.32, 4.65, 4.57, 4.13, 3.98; IR (diffuse reflectance) 2425, 2350, 2318, 2233, 1921, 1662, 1607, 1551, 1512, 1492, 1465, 1397, 1380, 1292, 809, cm$^{-1}$; MS (EI) m/z 411 (M$^+$), 244, 86, 84, 80, 79, 78, 65, 63, 61, 51; HRMS (FAB) calcd for $C_{21}H_{18}ClN_3O_4+H_1$ 412.1064, found 412.1067.

EXAMPLE 7
N-(4-Chlorobenzyl)-6-(3-hydroxypropyl)-7-methoxy-1-methyl-4-oxo-1,4-dihydro[1,8]naphthyridine-3-carboxamide

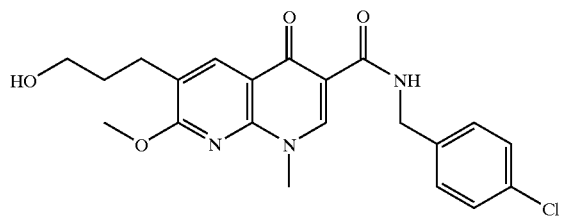

N-(4-Chlorobenzyl)-6-(3-hydroxy-1-propynyl)-7-methoxy-1-methyl-4-oxo-1,4-dihydro[1,8]naphthyridine-3-carboxamide (180 mg) is suspended in EtOH (50 mL) and $PtO_2$ is added. The mixture is shaken under an atmosphere of $H_2$ (45 psi) for 2 h. The solution is filtered through Celite, and concentrated in vacuo. The residue is purified by silica gel chromatography ($CH_2Cl_2$/MeOH 1/0, 45/1, 19/1) and recrystallyzed from MeOH to afford 55 mg of N-(4-chlorobenzyl)-6-(3-hydroxypropyl)-7-methoxy-1-methyl-4-oxo-1,4-dihydro[1,8]naphthyridine-3-carboxamide. Physical characteristics are as follows: $^1$H NMR (CDCl$_3$) δ10.49–10.46, 8.82, 7.35–7.30, 4.66, 4.12, 4.00, 3.71, 2.81, 1.98–1.88; IR (diffuse reflectance) 2350, 2317, 1940, 1921, 1916, 1663, 1617, 1568, 1550, 1516, 1456, 1397, 1385, 1283, 809, cm$^{-1}$; MS (EI) m/z 414 (M$^+$), 415, 276, 275, 249, 248, 246, 140, 84, 77, 57.

EXAMPLE 8
Ethyl 6-{[(4-chlorobenzyl)amino]carbonyl}-2-methoxy-8-methyl-5-oxo-5,8-dihydro[1,8]naphthyridine-3-carboxylate

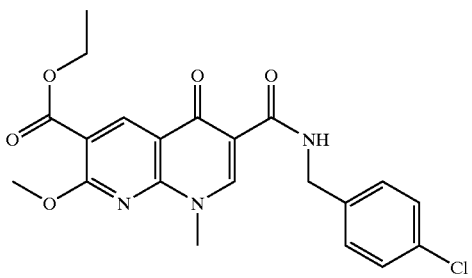

N-(4-Chlorobenzyl)-6-iodo-7-methoxy-1-methyl-4-oxo-1,4-dihydro[1,8]naphthyridine-3-carboxamide (700 mg), palladium acetate (32 mg), DPPP (60 mg), ethanol (10 mL) and triethylamine (1 mL) are dissolved in DMF (20 mL) in a steel bomb. The bomb is flushed with CO (3×) and then pressured with CO (400 psi) and the resulting reaction is stirred at 80° C. for 24 h, cooled to room temperature and diluted with $CH_2Cl_2$. The organic is washed with water, 1N HCl, brine, dried ($MgSO_4$), filtered and concentrated in vacuo. The residue is purified by silica gel chromatography ($CH_2Cl_2$/MeOH 1/0, 45/1) and then triturated with MeOH to afford 472 mg (76%) of ethyl 6-{[(4-chlorobenzyl)amino]carbonyl}-2-methoxy-8-methyl-5-oxo-5,8-dihydro[1,8]naphthyridine-3-carboxylate. Physical characteristics are as follows: $^1$H NMR (CDCl$_3$) δ10.26–10.23, 9.18, 8.85, 7.32, 4.65, 4.40, 4.19, 4.00, 1.41; $^{13}$C NMR (CDCl$_3$) δ176.33, 164.24, 163.76, 163.28, 150.17, 148.34, 142.24, 137.17, 132.94, 129.00, 128.73, 116.32, 113.96, 113.29, 61.57, 55.17, 42.86, 39.17, 14.24; IR (diffuse reflectance) 1965, 1727, 1663, 1609, 1568, 1542, 1514, 1493, 1466, 1390, 1297, 1260, 1141, 813, 799, cm$^{-1}$; MS (EI) m/z 429 (M$^+$), 431, 430, 429, 289, 263, 262, 261, 159, 140,77; Anal. calcd for $C_{21}H_{20}ClN_3O_5$: C, 58.68; H, 4.69; N. 9.77; Cl, 8.25. Found: C, 58.39; H, 4.70; N, 9.71.

Testing of Inventive Compounds

The antiviral activity of a compound of the invention can be determined using pharmacological models which are well known to the art, or using Test A described below.

The compounds of formula (III) and (IIIa) and pharmaceutically acceptable salts thereof are useful as antiviral agents. Thus, they are useful to combat viral infections in animals, including man. The compounds are generally active against herpes viruses, and are particularly useful against the varicella zoster virus (ZVZ), the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates.

The assay is conducted in 100 μl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. H$_2$O bath and terminated via the addition of 40 μl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula III in this assay are shown in Table 1. All results are listed as Polymerase IC$_{50}$ (μM) values. In Table 1, the term "nd" refers to activity data not determined.

| Example | HCMV | HSV | VZV |
|---------|------|-----|-----|
| 2 | 1.8 | 1.9 | 1.1 |
| 3 | 2.7 | 2.4 | 1.4 |
| 4 | 22.3 | nd | nd |
| 5 | 17.1 | nd | nd |
| 6 | 1.17 | nd | nd |
| 7 | 0.46 | nd | nd |
| 8 | 37% inhibition at 20 μM | nd | nd |

Having described the invention in detail and by reference to the preferred embodiments thereof, it will be apparent that modifications and variations are possible without departing from the scope of the appended claims.

What is claimed is:

1. A method for treating a disease or condition in a mammal caused by a viral infection, comprising administering to the mammal a therapeutically effective amount of a compound of formula III

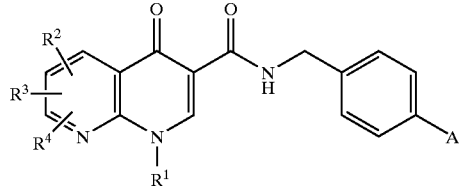

or a pharmaceutically acceptable salt thereof wherein,
A is
  (a) Cl,
  (b) Br,
  (c) CN,
  (d) NO$_2$, or
  (e) F;
R$^1$ is
  (a) R$^5$,
  (b) NR$^7$R$^8$, or
  (c) SO$_2$R$^9$;
R$^2$ is
  (a) aryl,
  (b) het,
  (c) SO$_m$R$^6$,
  (d) OC$_{2-7}$ alkyl substituted by OH,
  (e) SC$_{2-7}$ alkyl substituted by OH, or
  (f) C$_{2-8}$ alkyl which is partially unsaturated and is optionally substituted by one or more substituents selected from R$^{11}$, OR$^{13}$, SR$^{13}$, NR$^7$R$^8$, halo, (C=O)C$_{1-7}$ alkyl or SO$_m$R$^9$;
with the proviso that when R$^1$=R$^5$=(CH$_2$CH$_2$O)$_r$R$^{10}$, then R$^2$ may additionally represent
  (a) H,
  (b) halo,
  (c) (C=O)R$^6$,
  (d) (C=O)OR$^9$,
  (e) cyano,
  (f) OR$^{10}$,
  (g) Ohet,
  (h) NR$^7$R$^8$,
  (i) SR$^{10}$,
  (j) Shet,
  (k) NHCOR$^{12}$,
  (l) NHSO$_2$R$^{12}$, or
  (m) R$^2$ together with R$^3$ or R$^4$ form a carbocyclic or het which may be optionally substituted by NR$^7$R$^8$, or C$_{1-7}$alkyl which may be optionally substituted by OR$^{14}$;
R$^3$ and R$^4$ are independently:
  (a) H,
  (b) halo,
  (c) aryl,
  (d) S(O)$_m$R$^6$,
  (e) (C=O)R$^6$,
  (f) (C=O)OR$^9$,
  (g) cyano,
  (h) het, wherein said het is bound via a carbon atom,
  (i) OR$^{10}$,
  (j) Ohet,
  (k) NR$^7$R$^8$,
  (l) SR$^{10}$,
  (m) Shet,
  (n) NHCOR$^{12}$,
  (o) NHSO$_2$R$^{12}$,
  (p) C$_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$, or (q) $R^4$ together with $R^3$ form a carbocyclic or het which may be optionally substituted by $NR^7R^8$, or $C_{1-7}$alkyl which may be optionally substituted by $OR^4$;

$R^5$ is
(a) $(CH_2CH_2O)_iR^{10}$,
(b) het, wherein said het is bound via a carbon atom,
(c) aryl,
(d) $C_{1-7}$alkyl which may be partially unsaturated and is optionally substituted by one or more substituents selected from $NR^7R^8$, $R^{11}$, $SO_mR^9$, or $OC_{2-4}$alkyl which may be further substituted by het, $OR^{10}$, or $NR^7R^8$, or
(e) $C_{3-8}$cycloalkyl which may be partially unsaturated and optionally substituted by one or more substituents selected from $R^{11}$, $NR^7R^8$, $SO_mR^9$, or $C_{1-7}$alkyl optionally substituted by $R^{11}$, $NR^7R^8$, or $SO_mR^9$;

$R^6$ is
(a) $C_{1-7}$alkyl,
(b) $NR^7R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from $NR^{10}R^{10}$, $R^{11}$, $SO_mR^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl,
(d) methyl, or
(e) $C_{2-7}$alkyl which may be partially unsaturated and is optionally substituted by one or more substituents selected from $NR^{10}R^{10}$, $R^{11}$, SH, $CONR^{10}R^{10}$, or halo;

$R^{10}$ is
(a) H,
(b) methyl, or
(c) $C_{2-7}$alkyl optionally substituted by OH;

$R^{11}$ is
(a) $OR^{10}$,
(b) Ohet,
(c) Oaryl,
(d) $CO_2R^{10}$,
(e) het,
(f) aryl, or
(g) CN;

$R^{12}$ is
(a) H,
(b) het,
(c) aryl,
(d) $C_{3-8}$cycloalkyl,
(e) methyl, or
(f) $C_{2-7}$alkyl optionally substituted by $NR^7R^8$ or $R^{11}$ $R^{13}$ is
(a) $(P=O)(OR^{14})_2$,
(b) $CO(CH_2)_nCON(CH_3)-(CH_2)_nSO_3^{31}$ $M^+$,
(c) an amino acid,
(d) $C(=O)$aryl, or
(e) $C(=O)C_{1-7}$alkyl optionally substituted by $NR^7R^8$, aryl, het, $CO_2H$, or $O(CH_2)_nCO_2R^{14}$;

$R^{14}$ is
(a) H, or
(b) $C_{1-7}$alkyl;

each i is independently 2, 3, or 4;
each n is independently 1, 2, 3, 4 or 5;
each m is independently 0, 1, or 2;
M is sodium, potassium, or lithium;
aryl is a phenyl radical or an ortho-fused bicyclic carbocyclic radical wherein at least one ring is aromatic;
wherein any aryl is optionally substituted with one or more substituents selected from halo, OH, cyano, $CO_2R^4$, $CF_3$, $C_{1-6}$alkoxy, and $C_{1-6}$alkyl which may be further substituted by one to three $SR^{14}$, $NR^{14}R^{14}$, $OR^{14}$, or $CO_2R^{14}$ groups;
het is a four- (4), five- (5), six- (6), or seven- (7) membered saturated or unsaturated heterocyclic ring having 1, 2, or 3 hetero atoms selected from the group consisting of oxygen, sulfur, and nitrogen, which is optionally fused to a benzene ring, or any bicyclic heterocycle group;
wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$alkyl which may be further substituted by one to three $SR^{14}$, $NR^{14}R^{14}$, $OR^{14}$, or $CO_2R^{14}$ groups.

2. The method according to claim 1 wherein said viral infection is a herpes virus infection.

3. The method according to claim 1 wherein said mammal is a human.

4. The method according to claim 1 wherein said mammal is a livestock or companion animal.

5. The method according to claim 1 wherein the infection is herpes simplex virus type 1, 2, 6, 7, or 8, varicella zoster virus, human cytomegalovirus, or epstein-Barr virus.

6. The method according to claim 1 wherein the amount administered is from about 0.1 to about 300 mg/kg of body weight.

7. The method according to claim 1 wherein the amount administered is from about 1 to about 30 mg/kg of body weight.

8. The method according to claim 1 wherein the compound is administered parenterally, intravaginally, intranasally, topically, orally, or rectally.

* * * * *